(12) United States Patent
Keyhani

(10) Patent No.: US 6,328,467 B1
(45) Date of Patent: Dec. 11, 2001

(54) METHOD AND APPARATUS FOR DETECTING ICE OR FROST DEPOSITION

(75) Inventor: Majid Keyhani, Knoxville, TN (US)

(73) Assignee: University of Tennessee Research Corp., Knoxville, TN (US)

( * ) Notice: Subject to any disclaimer, the term of this patent is extended or adjusted under 35 U.S.C. 154(b) by 0 days.

(21) Appl. No.: 09/307,462

(22) Filed: May 7, 1999

(51) Int. Cl.$^7$ ........................................... G01N 25/02
(52) U.S. Cl. ............................................. 374/16; 374/25
(58) Field of Search .......................................... 374/16, 25

(56) References Cited

U.S. PATENT DOCUMENTS

| | | | |
|---|---|---|---|
| 3,594,775 | * | 7/1971 | Fox ........................................ 364/557 |
| 3,596,264 | * | 7/1971 | Ciemochowski ................ 340/870.16 |
| 4,333,004 | * | 6/1982 | Forgue et al. ........................ 219/497 |
| 4,671,072 | * | 6/1987 | Starck et al. ............................ 62/140 |
| 4,766,369 | * | 8/1988 | Weinstein ............................. 324/670 |
| 4,808,009 | * | 2/1989 | Sittler et al. ........................... 374/178 |
| 4,980,673 | * | 12/1990 | Kleven ................................. 340/581 |
| 4,981,369 | * | 1/1991 | Kumada et al. ........................ 374/16 |
| 5,140,135 | * | 8/1992 | Freeman ............................... 219/497 |
| 5,345,223 | * | 9/1994 | Rutkiewics ........................... 340/581 |
| 5,398,547 | * | 3/1995 | Gerardi et al. ..................... 73/170.26 |
| 5,497,100 | * | 3/1996 | Reiser et al. .......................... 324/643 |
| 5,709,470 | | 1/1998 | Finley . |
| 5,730,026 | | 3/1998 | Maatuk . |
| 5,790,026 | * | 8/1998 | Lardiere et al. ...................... 340/581 |
| 5,908,985 | * | 6/1999 | Maatuk ................................. 73/295 |

* cited by examiner

*Primary Examiner*—Diego Gutierrez
*Assistant Examiner*—Lydia M De Jesús
(74) *Attorney, Agent, or Firm*—Akerman, Senterfitt & Eidson, P.A.

(57) ABSTRACT

A method and system for detecting the presence of a frozen deposition at an interface between a substrate of known thermophysical properties and surroundings of unknown thermophysical properties. The system involves applying a predetermined quantity of heat to a temperature sensor positioned at the interface to cause a thermal perturbation, measuring an output signal of the sensor subsequent to applying the predetermined quantity of heat, and comparing one or more measured values of the output signal to one or more reference output level values to determine the presence or absence of the frozen deposition.

14 Claims, 5 Drawing Sheets

METHOD AND APPARATUS FOR DETECTING ICE OR FROST DEPOSITION

BACKGROUND OF THE INVENTION

1. Field of the Invention

This invention concerns the field of environmental sensors, and more particularly a sensor for detecting the buildup of frost or ice.

2. Description of the Related Art

Moisture condenses onto a surface whose temperature is cooled below the air's dew point. If the surface temperature is freezing then a frost or ice layer forms and gradually thickens with time. This deposition of frost can have detrimental effects on the operation of machinery which is operated outdoors. For example, frost on refrigeration coils is known to degrade the efficiency of refrigeration machines and can compromise reliable operation of the equipment.

In addition to the efficiency concerns raised by ice buildup, the icing of airplane wings is a major safety concern for the aviation industry because of the sudden loss of lift caused by wing icing can lead to catastrophic accidents. Similarly, frost deposits on roadways can be a serious safety hazard. For example ice formation on roadways, bridges and overpasses is the cause of many automobile accidents. The risk of such automobile and aircraft accidents may be minimized if it were possible to provide drivers and pilots with some warning of the hazardous condition which exists in each case.

HVAC manufacturers limit the ill effect of frosting by using an inexpensive and reliable time-and-temperature defrost control. However, such controls suffer from a drawback in that they require an adaptive logic because the sensors do not directly measure the frost buildup. For example, HVAC manufacturers use detectors that measure the increase in air pressure drop across the refrigeration coil or in another scheme they measure the temperature gradient from the refrigeration coil to the surrounding ambient air temperature. However, these measures are known to suffer from the false indications of frost buildup in inclement weather.

Other embodiments of sensors proposed for refrigeration are based on ultrasonic, emissivity and photo cell technologies.

In the transportation and aviation industries, several techniques are available for detecting an icing condition of a road or wing section. As an example, such sensors have been known to employ a network of thin, flexible microstrip antennas, distributed on aircraft wing, to measure the unique electrical properties of compounds that accumulate on the wing surface. Temperature and acoustic data is gleaned and processing of data shows the presence or absence of ice. Another known ice sensing technique uses a temperature sensor and a parallel arrangement of electrodes whose coefficient of coupling is indicative of the formation of ice. Still another technique applies a controlled heat to a sensing element which when dry displays a linear time-temperature curve. Ice or frost modifies the sensing element's time-temperature curve and the shift in the curve is used to indicate an icy road condition.

As noted above, existing frost sensors used in refrigeration do not directly detect the buildup of frost. They sense the pressure drop through the coil or the temperature gradient from the outdoor-ambient air to the refrigerant. Optical, ultrasonic and emissivity technologies use the effect of sound or electromagnetic radiation in their respective detection schemes. In both transportation and aviation, the detection schemes measure the temperature and either measure the electrical, acoustic or heat transfer characteristics from some sensing element.

SUMMARY OF THE INVENTION

The proposed sensor uses thermocouples or other heat sensor whose time-temperature history reveal the formation of frost or ice because of a change in the thermal properties of its surroundings. No form of electromagnetic radiation, nor any optical system is needed for detection.

According to one aspect of the invention, the method involves a series of steps including: applying a predetermined quantity of heat to a temperature sensor positioned at the interface to cause a thermal perturbation; measuring an output signal of the sensor subsequent to the applying step; and comparing a measured value of the output signal to a reference value to determine the presence of the frozen deposition.

The measuring step can be accomplished by recording two or more measured output values defining a transient response curve, and comparing the transient response curve to a reference transient response curve. The transient curve advantageously includes at least that portion of the transient curve defining a thermal decay response for the sensor.

According to another aspect of the invention, the predetermined quantity of heat applied to the sensor can be defined as the maximum quantity of heat required under the coldest anticipated operating conditions to raise the sensor temperature above a freezing temperature, except when the frozen deposition is present at the interface. In this embodiment, the predetermined quantity of heat applied to the sensor is determined based on a variety of criteria which can include a minimum anticipated operating temperature of the surroundings, a maximum anticipated wind velocity and the thermophysical properties of the substrate. The scientific basis for this embodiment is that the predetermined quantity of applied heat is not sufficient to affect a phase change, i.e., change ice to water. Therefore, the if ice is present temperature of the heated sensor will not rise above freezing temperature of water.

The temperature sensor may be any of a variety of commercially available temperature sensor units which have an electronically readable output. The heat applied to the sensor can be provided by an integrated heating device formed as part of the sensor or a separate heating element provided for this purpose. According to a preferred embodiment, the temperature sensor is a thermocouple device so that by passing a current through the thermocouple, it can be heated without the need for a separate heater unit.

A system for carrying out the foregoing method can be formed with a temperature sensor positioned at the interface to cause a thermal perturbation; a heater element is provided for applying a predetermined quantity of heat to the temperature sensor. However the heater element may be combined with the sensor for instance when a thermocouple is used for this purpose. Electronic circuitry is provided for measuring an output signal of the sensor and for comparing one or more measured value of the output signal after application of the predetermined quantity of heat to one or more corresponding reference values. Where the measured values match the reference values obtained for the presence of the frozen deposition, a suitable display or audible warning device may be provided to notify a user. Alternatively, a signal indicating the presence of ice can be used to control a related piece of equipment to respond to the presence of such ice.

The electronic circuitry or software for measuring can include suitable equipment for recording a set of measured output values defining a transient response curve. Additional circuitry or software can also be included to compare the transient response curve to a reference transient response curve. According to one aspect, the transient response curve represents a thermal decay time.

As with the method previously described, the predetermined quantity of heat applied to the sensor can be defined as the maximum quantity of heat required under the coldest anticipated operating conditions to raise the sensor temperature above a freezing temperature, except when the frozen deposition is present at the interface. In that case the predetermined quantity of heat applied to the sensor is determined based on criteria which can include factors such as the minimum anticipated operating temperature of the surroundings, the maximum anticipated wind velocity and the thermophysical properties of the substrate on which the sensor is mounted. The scientific basis for this embodiment is that the predetermined quantity of applied heat is not sufficient to affect a phase change, i.e., change ice to water. Therefore, the temperature of the heated sensor will not rise above freezing temperature of water.

The temperature sensor used with the system can be any of a variety of commercially available temperature sensor units which have an electronically readable output. Likewise, the heat applied to the sensor can be provided by an integrated heating device formed as part of the sensor or a separate heating element provided for this purpose. According to a preferred embodiment, however, the temperature sensor is a thermocouple or RTD device so that heat can be applied to the sensor without the need for a separate heater unit. dr

DETAILED DESCRIPTION OF THE PREFERRED EMBODIMENTS

Figure 1:
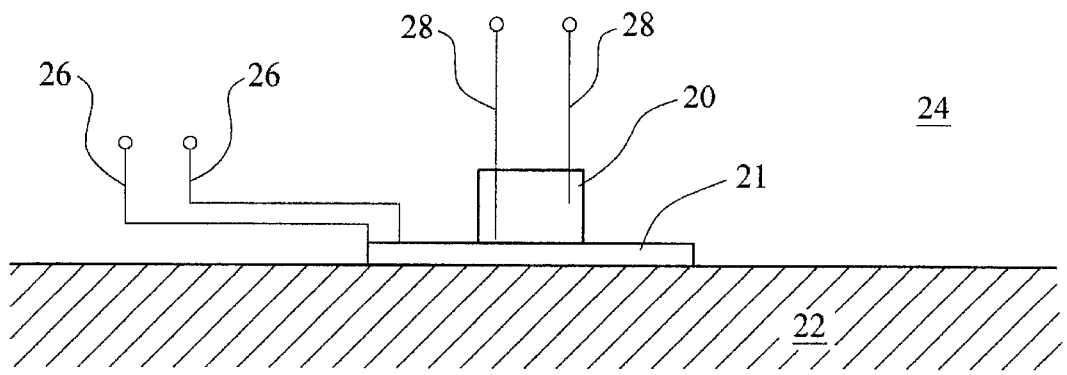
FIG. 1 is a schematic diagram showing a sensor placed at the interface of a substrate with known thermophysical properties and a surrounding environment whose thermophysical properties are unknown.

FIG. 1 shows a temperature sensor 20 positioned at the interface of a substrate 22 having known thermophysical properties and a surrounding 24 whose thermophysical properties are unknown. Suitable means are provided for causing a thermal perturbation of the sensor 20. For example a heater 21 can be provided for this purpose. If the heater 21 is of the electrical type, it can be provided with electrical leads 26 for applying heat energy to the sensor. However, the invention is not limited in this regard and any suitable heating element can be used which is capable of causing a thermal perturbation, provided that the heating element 21 is preferably located beneath the sensor so that the surface of the sensor remains exposed to the surroundings 24.

Figure 2:
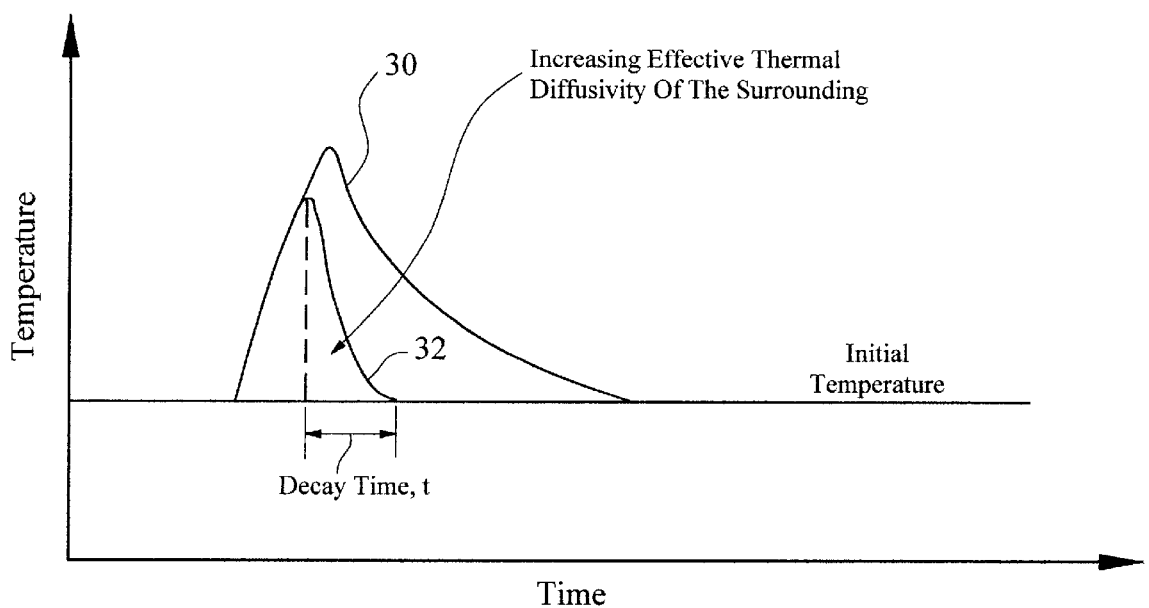
FIG. 2 is a graphical representation showing thermal decay times with and without the presence of a frozen deposition such as water.

Alternatively, depending on the type of sensor, a thermal perturbation can be achieved without the need for a separate heater element 21. For example, if the sensor is comprised of a thermocouple or a Resistive Temperature Device (RTD), then an electrical current of known value and duration can be applied directly to the leads 28 of the sensor element so as to cause a pre-determined thermal perturbation of the sensor element 20. In any case, the known thermal perturbation created by temporarily heating the sensor 20 results in a temporary increase in the measured temperature output for the sensor 20 and then a gradual decay as the temperature returns to ambient conditions. An example of this transient response resulting from the thermal perturbation is shown in FIG. 2.

The transient response of sensor 20 to the thermal perturbation will depend upon a variety of factors but most significantly upon the effective thermal diffusivity of the surroundings 24 and the substrate 22. Significantly, however, if the substrate is known, then any significant variations in the transient response can be attributed to the surroundings. This concept is illustrated in FIG. 2 by two distinct response curves 30 and 32. As shown in FIG. 2, the thermal decay time $\tau$, will vary depending on the effective thermal diffusivity of the surroundings 24. For example, the rate of temperature decay in sensor 20 surrounded by ice will be substantially more rapid as compared to a sensor surrounded by air. Likewise, the decay time with ice is also more rapid as compared to chilled water because the thermal diffusivity of ice is about seven times larger than that of chilled water. The rapid decay when the sensor is surrounded by ice can be attributed largely to the shift in the heat transfer mechanism from convection to air to conduction in ice which occurs in the presence of ice.

Figure 4:
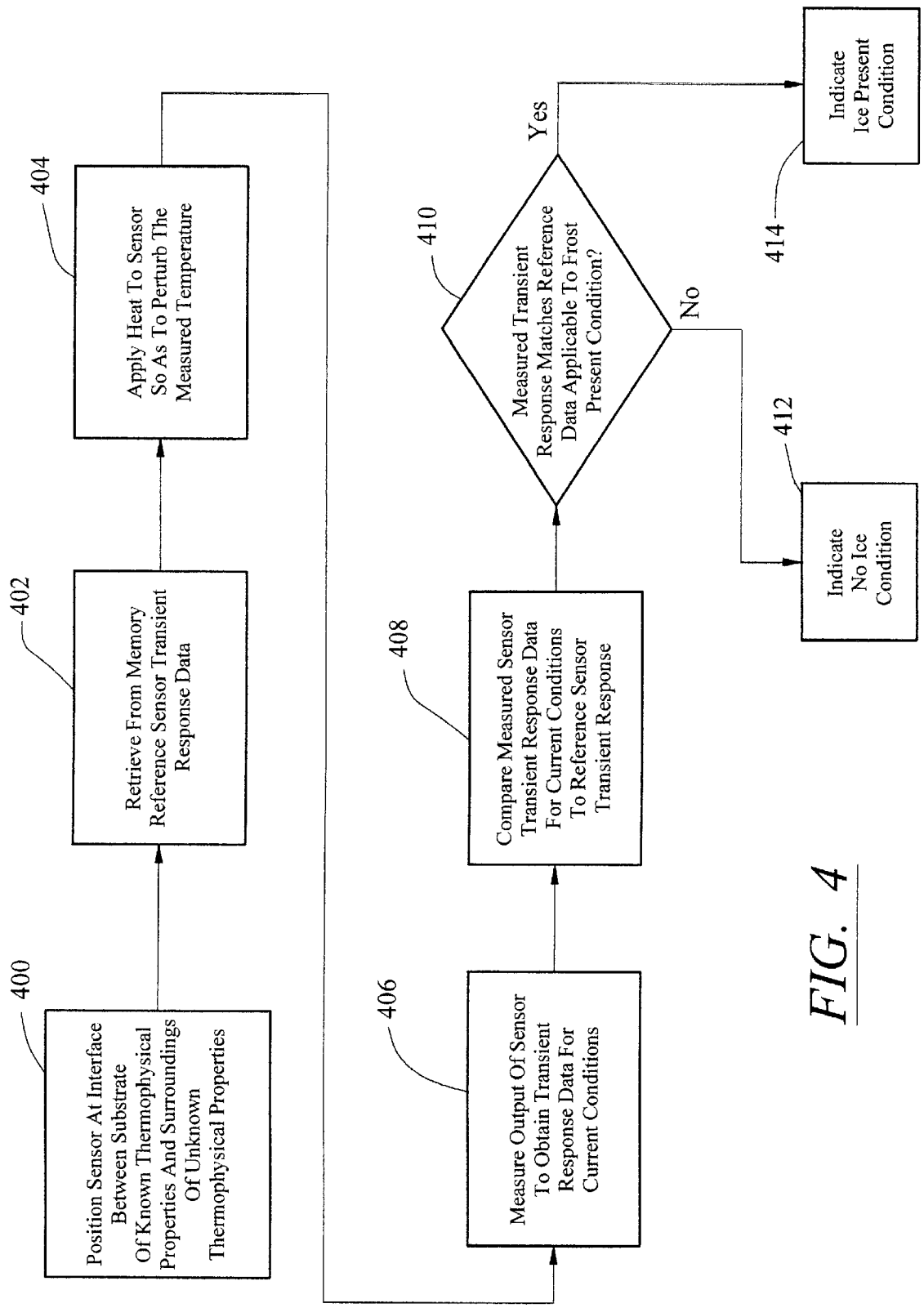
FIG. 4 is a flow chart showing the process according to a first embodiment of the invention.

The different transient response and/or decay times associated with various surroundings as described herein can be used as a signature to identify the presence or absence of a frozen deposition such as ice. In particular, reference or baseline transient responses can be obtained under known operating conditions with the sensor 20 mounted to a known substrate material 22 which has the same thermal diffusion characteristics as the substrate on which the sensor is intended to be used in practice. Subsequently, such reference or baseline response "signatures" can be related to identify unknown surroundings under operational conditions. Thus, if reference data is obtained for the transient/decay response in the presence and in the absence of ice (or any other frozen deposition) and with the sensor mounted to the substrate for which it is intended to be used in practice, then this reference data can subsequently be associated to transient/decay responses where the presence or absence of frost is to be determined. The foregoing process is illustrated by steps 400 through 414 in flow chart form in FIG. 4.

Any suitable temperature sensor can be used for carrying out the method as described herein. In a preferred embodiment, however, the temperature sensor is a thermocouple. In the embodiment without the heating element 21, an electrical current is applied for a short period of time to the thermocouple itself so that it causes resistive heating of the device. Once the electric current is removed, the thermocouple begins to return to its ambient temperature and the desired transient response is obtained. Other devices which may be used to similar effect are resistive temperature devices ("RTD's") which are conventionally used as temperature sensors.

Figure 5:
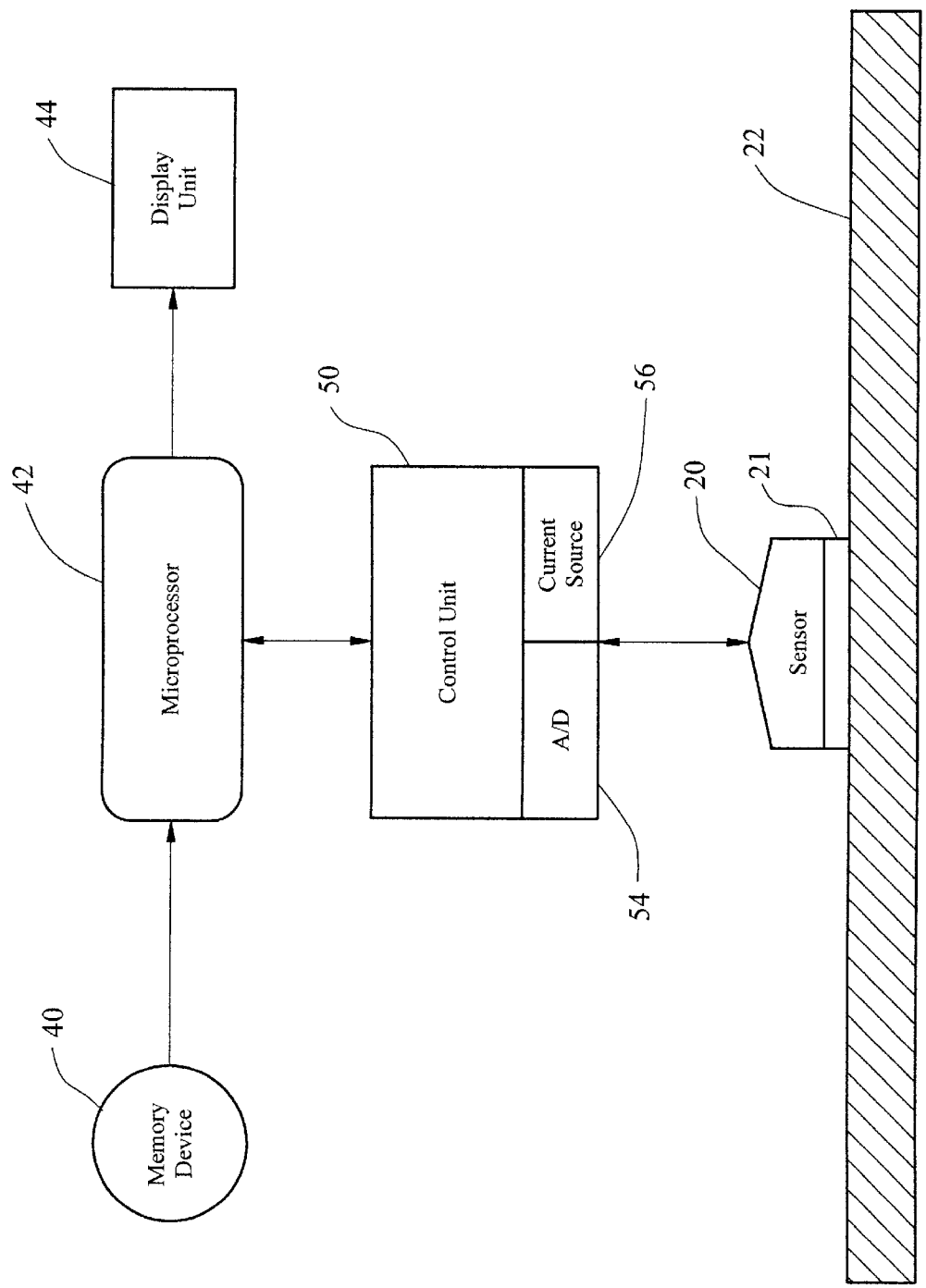
FIG. 5 is a block diagram showing a system for determining the presence of a frozen deposition on a substrate of known thermophysical properties.

FIG. 5 is a block diagram showing the basic operation of a frozen deposition detection system according to a preferred embodiment of the invention. As shown in FIG. 5, the system according to the invention is preferably controlled by microprocessor 42 and includes a control unit 50. Control unit 50 preferably incorporates an analog to digital ("A/D") converter 54 for converting the analog voltage output of sensor 20 to a digitized representation which may be used as an input to the microprocessor. A current source 56 is preferably provided as part of the control unit 50. Upon command from the microprocessor, the current controller 56 causes an electric current to flow so as to apply a thermal perturbation. If a thermocouple or RTD unit is used for the sensor 20, the electric current can be applied directly to the sensor leads for a heating effect and no separate heater element 21 is required. Alternatively, if other another type of sensor not capable of direct heating is used then the current is preferably applied to the heater unit 21. In any case, the application of the predetermined quantity of heat results in a transient response as discussed relative to FIG. 2. The current is then removed and the sensor output is measured via A/D converter 54 to obtain the transient/decay response. This response is compared by the microprocessor 42 to the reference transient previously recorded for the particular type sensor under controlled conditions with the same substrate 22. The microprocessor uses this information to evaluate whether the measured response matches the response expected for the presence of ice or the absence of ice. The comparison can be made on a data-point by data-point basis to evaluate how closely the curves match, can involve a comparison of the measured decay time to a reference value, or any other suitable means for matching the characteristics of the measured transient response to the reference transient response. In any case, the results can then be communicated to a user by suitable means such as by displaying a message on display unit 44. If the transient or decay response matches the reference response for ice present, then the display will indicate the presence of ice.

It will be readily appreciated by those skilled in the art that numerous alternative embodiments of the invention are also possible. For example, the microprocessor 42 and control unit could be replaced by conventional analog circuitry capable of comparing a measured transient response to a reference. However, it will likewise be appreciated that the programmable microprocessor arrangement shown in FIG. 5 allows for greater flexibility when using different types of sensors on various different substrates.

Figure 6:
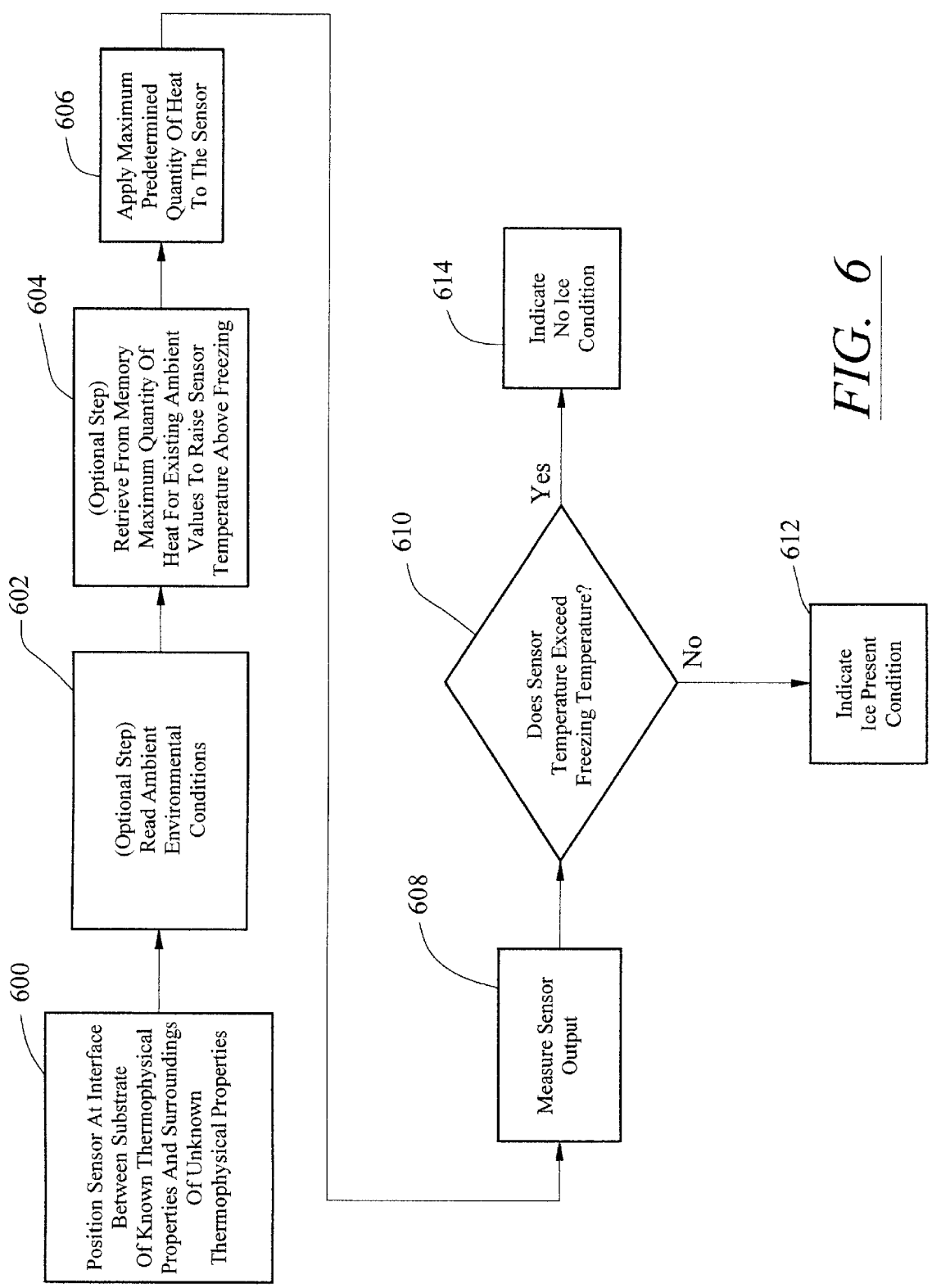
FIG. 6 is a flow chart showing the process according to a second embodiment of the invention.

According to an alternative embodiment of the invention, it is also possible to detect the presence of a frozen deposition such as ice by taking advantage of the required latent heat which is needed to affect a phase change. The process by which this result may be achieved is illustrated in FIG. 6, steps 600–614. Latent heat is the quantity of heat absorbed or released by a substance undergoing a change of state or phase. For example, such a state or phase change occurs when ice transitions to water, or water transitions to steam. In this method, it is necessary first to establish the maximum quantity of applied heat that is required to raise the temperature of the sensor 20 above the temperature at which the deposition solidifies or freezes. In the case of water, this would be thirty-two degrees Fahrenheit. For convenience this temperature shall hereinafter generically be referred to as the freezing temperature, it being understood however, that the freezing temperature could differ in the case of different materials.

In any case, this so called maximum quantity of applied heat will take into account the coldest anticipated operating temperature which the sensor is likely to encounter, the thermal diffusivity of the substrate material on which the sensor is mounted, and any other heat loss mechanisms such as anticipated airflow velocity over the sensor in the absence of the ice or other frozen deposition. This maximum value of applied heat can be determined either experimentally or by calculation so that when such quantity of heat is delivered to the sensor 20, it will have the effect of raising the temperature of the sensor above freezing for all operating conditions where no ice or other frozen deposition is surrounding the sensor. For many applications it will be sufficient to simply define the maximum quantity of applied heat based on the coldest temperature likely to be encountered by the sensor.

Those skilled in the art will recognize that for certain applications, it may be appropriate to account for other heat loss mechanisms such as wind velocity for the purpose of establishing a set of maximum quantity of applied heat values. Thus, in FIG. 6, optional step 602 includes reading of ambient environmental conditions such as ambient temperature, humidity and wind velocity, and at step 604 selecting a maximum heat quantity based on the given ambient environmental conditions. The sensor 20 will typically be incapable of sensing anything other than temperature. However, in many applications, the ambient conditions can be obtained from other sensors associated with the equipment. For example, in the case of aircraft wings, ambient temperature, wind velocity and humidity conditions can be obtained from other sensors on board an aircraft. Most applications will not require these additional ambient conditions to be addressed so that only a single maximum heat quantity need be determined and applied.

Once the maximum applied heat requirement is determined, the application of that quantity of heat to the sensor will result in a response that will always raise the sensor temperature above the freezing temperature, at least momentarily, when no frozen deposition or ice is present. Significantly, however, for the case where ice or some other frozen deposition surrounds the sensor, the application of the predetermined maximum quantity of heat would result in a response that will not cause the sensor temperature to surpass the freezing temperature. This failure to raise the temperature above the freezing temperature is due to the additional energy that is always required in order to effect a state change for a frozen deposition such as ice.

Figure 3:
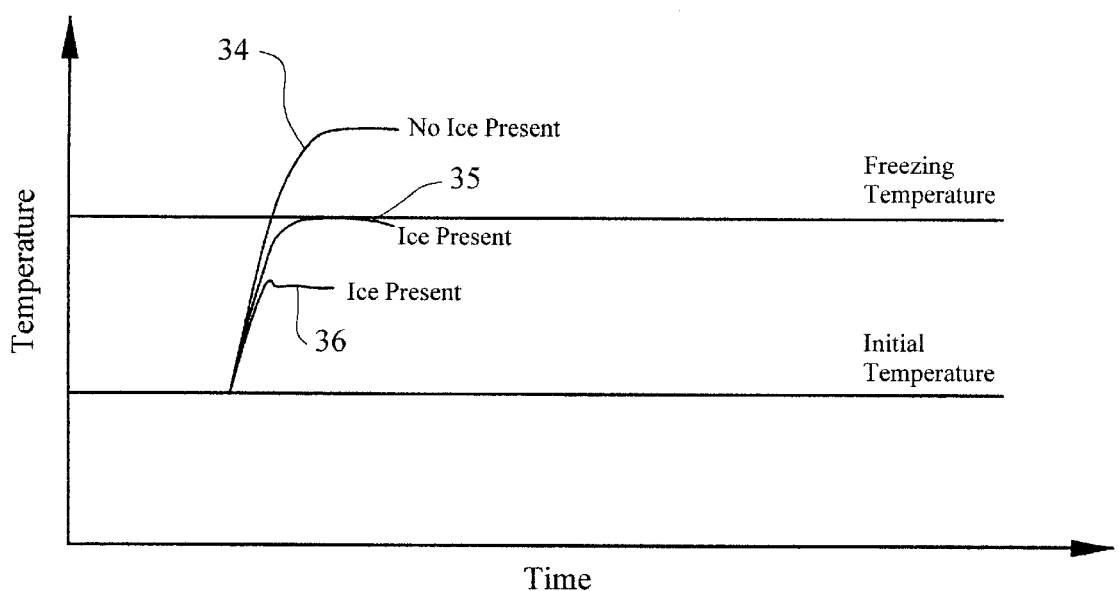
FIG. 3 is a graphical representation showing temperature rises caused by energy applied to a temperature sensor in the presence of a frozen deposition and in the absence of such frozen deposition.

FIG. 3 illustrates graphically the temperature response of a sensor 20 versus time when the maximum quantity of heat is applied as described above. As shown in curve 34 of FIG. 3, the application of such heat where no ice is present raises the sensor temperature above the freezing temperature. However, the application of the same amount of heat fails to raise the temperature above freezing as shown by curves 35 and 36 when ice is present. This is due to the fact that the amount of energy input to the sensor 20 is not sufficient to affect a phase change. Accordingly, the additional energy applied to the sensor 20 in the form of heat is absorbed by the surrounding ice or frost without any corresponding rise in temperature above freezing temperature. The foregoing method is advantageous as it does not require any transient signature analysis. Instead, it is merely necessary to detect a measured temperature response below or at freezing temperature to indicate the presence of ice on the sensor. In order to implement the foregoing system, an arrangement similar to that shown in FIG. 5 can be used.

It will be recognized by those skilled in the art that the method according to FIG. 6 avoids the need for complex transient signature analysis. Thus, the control circuitry and programming for this alterative method can potentially be simplified to some extent as compared to FIG. 5. The delivery of the maximum required heat to the sensor can be accomplished by various means depending upon the type of sensor which is used. Once again, the use of a thermocouple as a sensor element is preferred due to the fact that the thermocouple can serve as both a heating and sensing element. In the case of the thermocouple sensor or RTD sensor, the heat can be applied directly by connecting an electric current of predetermined amperage and duration, Alternatively, an auxiliary heating device 21 may be used as previously described relative to FIG. 1.

While the foregoing specification illustrates and describes the preferred embodiments of this invention, it is to be understood that the invention is not limited to the precise construction herein disclosed. The invention can be embodied in other specific forms without departing from the spirit or essential attributes. Accordingly, reference should be made to the following claims, rather than to the foregoing specification, as indicating the scope of the invention.

I claim:

1. A method for detecting the presence of a frozen deposition at an interface between a substrate of known thermophysical properties and surroundings of unknown thermophysical properties comprising the steps of:

applying a predetermined quantity of heat to a temperature sensor positioned at said interface to cause a thermal perturbation without melting said frozen deposition if present;

measuring at least one output signal of said sensor subsequent to said applying step, said output signal being a function of the temperature of said sensor;

comparing at least one measured value of said output signal to at least one reference value to determine the presence of said frozen deposition.

2. The method according to claim 1 wherein said measuring step further comprises a step of recording a plurality of measured output values defining a transient response curve.

3. The method according to claim 2 wherein said comparing step further comprises a step of comparing said transient response curve to a reference transient response curve.

4. The method according to claim 3 wherein said transient response curve represents a thermal decay time.

5. The method according to claim 1 wherein said predetermined quantity of heat applied to said sensor is determined based on criteria which include at least one of a minimum anticipated operating temperature of said surroundings, a maximum anticipated wind velocity and the thermophysical properties of said substrate.

6. The method according to claim 1 wherein said sensor is selected from the a group consisting of a thermocouple and a resistive temperature device.

7. A method for detecting the presence of a frozen deposition at an interface between a substrate of known thermophysical properties and surroundings of unknown thermophysical properties, comprising the steps of:

determining a maximum quantity of heat required under a coldest anticipated operating condition to raise a sensor to a temperature above a freezing temperature, except when said frozen deposition is present at said interfaces;

applying said maximum quantity of heat to said sensor, and measuring at least one output signal of said sensor subsequent to said applying step, said output signal being a function of the temperature of said sensor, wherein a measured response corresponding to a temperature below a freezing temperature after application of said maximum quantity of heat to said sensor indicates a presence of said frozen deposition.

8. A system for detecting the presence of a frozen deposition at an interface between a substrate of known thermophysical properties and surroundings of unknown thernophysical properties comprising:

a temperature sensor positioned at said interface to receive a thermal perturbation;

means for applying a predetermined quantity of heat to said temperature sensor, said predetermined quantity of heat insufficient to melt said frozen deposition if present;

means for measuring an output signal of said sensor, said output signal being a function of the temperature of said sensor;

means for comparing at least one measured value of said output signal after application of said predetermined quantity of heat to at least one reference value to determine the presence of said frozen deposition.

9. The system according to claim 8 wherein said means for measuring further comprises a means for recording a plurality of measured output values defining a transient response curve.

10. The system according to claim 9 wherein said comparing means further comprises a means for comparing said transient response curve to a reference transient response curve.

11. The system according to claim 10 wherein said transient response curve represents a thermal decay time.

12. The system according to claim 8 wherein said predetermined quantity of heat applied to said sensor is defined as a maximum quantity of heat required under a coldest anticipated operating condition to raise the sensor temperature above a freezing temperature, except when said frozen deposition is present at said interface.

13. The system according to claim 8 wherein said predetermined quantity of heat applied to said sensor is determined based on criteria which include at least one of a minimum anticipated operating temperature of said surroundings, a maximum anticipated wind velocity and the thermophysical properties of said substrate.

14. The system according to claim 8 wherein said sensor is selected from the group consisting of a thermocouple and a resistive temperature device.

* * * * *